US007879905B2

(12) United States Patent
Klimko et al.

(10) Patent No.: US 7,879,905 B2
(45) Date of Patent: Feb. 1, 2011

(54) 5,6,7-TRIHYDROXYHEPTANOIC ACID AND ANALOGS FOR THE TREATMENT OF OCULAR DISEASES AND DISEASES ASSOCIATED WITH HYPERPROLIFERATIVE AND ANGIOGENIC RESPONSES

(75) Inventors: Peter G. Klimko, Fort Worth, TX (US); Mark R. Hellberg, Arlington, TX (US); David P. Bingaman, Weatherford, TX (US); Daniel A. Gamache, Arlington, TX (US)

(73) Assignee: Alcon, Inc., Hunenberg (CH)

( * ) Notice: Subject to any disclaimer, the term of this patent is extended or adjusted under 35 U.S.C. 154(b) by 1324 days.

(21) Appl. No.: 11/268,968

(22) Filed: Nov. 8, 2005

(65) Prior Publication Data

US 2006/0099248 A1 May 11, 2006

Related U.S. Application Data

(60) Provisional application No. 60/626,209, filed on Nov. 9, 2004.

(51) Int. Cl.
*A61K 31/38* (2006.01)
*A61K 31/19* (2006.01)
*A01N 37/02* (2006.01)
(52) U.S. Cl. .................. 514/460; 514/546; 514/558
(58) Field of Classification Search ................ 514/460, 514/546, 558
See application file for complete search history.

(56) References Cited

U.S. PATENT DOCUMENTS

| 4,771,042 A | 9/1988 | Braughler et al. |
| 4,975,537 A | 12/1990 | Aristoff et al. |
| 5,441,951 A | 8/1995 | Serhan et al. |
| 6,627,658 B2 | 9/2003 | Serhan et al. |
| 2002/0037929 A1 | 3/2002 | Kapin et al. |

FOREIGN PATENT DOCUMENTS

| JP | 08268886 A2 | 10/1996 |
| WO | WO 2005/112905 A1 | 12/2005 |

OTHER PUBLICATIONS

Crum et al., A New Class of Steroids Inhibits Angiogenesis in the Presence of Heparin or a Heparin Fragment, Science, vol. 230:1375-1378, Dec. 20, 1985.
Fierro et al., J. Pharm. Expt. Ther., 300(2), 385-392, (2002).
Folkman et al., Angiostatic Steroids, Ann. Surg., vol. 206(3), 374-383 (1987).
Ingber et al., A Possible Mechanism for Inhibition of Angiogenesis by Angiostatic Steroids: Induction of Capillary Basement Membrane Dissolution, Endocrinology vol. 119:1768-1775 (1986).
Lee et. al., Biochemical and Biophysical Research Communications, 180(3), 1416-1421 (1991).
Li et al., Angiostatic Steroids Potentiated by Sulphated Cyclodextrin Inhibit Corneal Neovascularization, Investigative Ophthalmology and Visual Science, vol. 32(11):2898-2905, (Oct. 1991).
Morgan and Valnio, Non-steroidal anti-inflammatory durgs and cancer prevention: a review of the recent evidence, Current Topics in Pharmacology, 6, 25-39 (2002).
PCT Intl Search Report for PCT/US2005/040392 mailed Mar. 21, 2006.
PCT Written Opinion for PCT/US2005/040392 mailed Mar. 21, 2006.
Serhan CN et al., Clin. Chem. Lab. Med, 37, 299-309 (1999).
Serhan CN. et. al., J. Pharmacol. Exp. Ther. 287, 779-790 (1998).
Sharma et al, A Quantitative Angiogenesis Model for Efficacy Testing of Chemopreventive Agents, Anticancer Research, 21(6A), 3829-3837 (2001).
Shiff and Rigas, Nature Medicine (New York), 5(12), 1348-1349 (1999).
Jones, R., et al., Corticosteroid-induced ocular hypertension and glaucoma: a brief review and update of the literature, Curr. Opin. Ophthalmol. 2006, pp. 163-167, vol. 17, Lippincott, Williams & Wilkins.
Hagihara, et al., Role of inflammatory responses in initiation of atherosclerosis: effects of anti-inflammatory drugs on cuff-induced leukocyte accumulation and intimal thickening of rabbit carotid artery, Atherosclerosis, 1991, pp. 107-116, vol. 91.
Tsurufuji, et al., Dexamethasone Inhibits Generation in Inflammatory Sites of the Chemotactic Activity Attributable to Leukotriene B4, Biochem. Biophys, Res. Commun., 1984, pp. 884-890, vol. 119(3).
Yadav, et al., Stereoselective Total Synthesis of 5(S),6(R),15(S)-Trihydroxy-7(E),9(E),11(Z),13(E)-Eicosatetraenoic Acid (Lipoxin A), 1998, pp. 143-146, vol. 39(1/2).
John L. Wallace, et al., "Lipoxins in gastric mucosal health & disease," Prostaglandins, Leukotrienes and Essential Fatty Acids, 2005, pp. 251-255, vol. 73.
Mark J. Paul-Clark, et al., "15-epi-lipoxin A4-mediated Induction of Nitric Oxide Explains How Aspirin Inhibits Acute Inflammation," J. Exp. Med., Jul. 5, 2004, pp. 69-78, vol. 200, No. 1.
Jun Tamaoki, et al., "Lipoxin A4 inhibits cholinergic neurotransmission through nitric oxide generation in the rabbit trachea," European Journal of Pharmacology, 1995, pp. 233-238, vol. 287.
Brett M. Mitchell, MS, "Impaired Vasodilation and Nitric Oxide Synthase Activity in Glucocorticoid-Induced Hypertension," Biological Research for Nursing, Jul. 2002, pp. 16-21, vol. 4, No. 1.
Karsten Gronert, et al., "A Role for the Mouse 12/15-Lipoxygenase Pathway in Promoting Epithelial Wound Healing and Host Defense," The Journal of Biological Chemistry, Apr. 15, 2005, pp. 15267-15278, vol. 280, No. 15.
Gronert, et al., "Selectivity of Recombinant Human Leukotriene D4, Leukotriene B4, and Lipoxin A4 Receptors with Aspirin-Triggered 15-epi-LXA4 and Regulation of Vascular and Inflammatory Responses," American Journal of Pathology, Jan. 2001, pp. 3-9, vol. 158, No. 1.
Fiore, et al., "Induction of Functional Lipoxin A4 Receptors in HL-60 Cells," Blood, Jun. 15, 1993, pp. 3395-3403, vol. 81, No. 12.
Chiang, et al., "The Lipoxin Receptor ALX: Potent Ligand-Specific and Stereoselective Actions in Vivo,"Pharmacology Reviews, 2006, pp. 463-487, vol. 58, No. 3.

*Primary Examiner*—Gollamudi S Kishore
*Assistant Examiner*—Adam Milligan
(74) *Attorney, Agent, or Firm*—Jason J. Derry

(57) ABSTRACT

Compositions containing 5,6,7-trihydroxyheptanoic acid and analogs and their use for treating posterior segment ocular diseases and diseases characterized by cellular hyperproliferation or angiogenesis, are disclosed.

1 Claim, No Drawings

5,6,7-TRIHYDROXYHEPTANOIC ACID AND ANALOGS FOR THE TREATMENT OF OCULAR DISEASES AND DISEASES ASSOCIATED WITH HYPERPROLIFERATIVE AND ANGIOGENIC RESPONSES

This application claims priority from the provisional application, U.S. patent application Ser. No. 60/626,209 filed Nov. 9, 2004.

The present invention is directed to 5,6,7-trihydroxyheptanoic acid and analogs and their methods of use, including in ophthalmic compositions. The compounds are particularly useful in treating persons suffering from posterior segment ocular diseases such as diabetic retinopathy and age-related macular degeneration, and disorders characterized by cellular hyperproliferation and angiogenesis, such and as rheumatoid arthritis, coronary artery restenosis after balloon angioplasty, and cancer.

BACKGROUND OF THE INVENTION

Conditions characterized by cellular hyperproliferation, such as chronic inflammation, ischemic diseases, and cancer are often accompanied by intense angiogenesis, a highly orchestrated process involving vessel sprouting, endothelial cell migration, proliferation, and maturation. Endothelial cells are normally quiescent but become activated during the angiogenic response. Upon stimulation, endothelial cells can degrade their basement membrane and proximal extracellular matrix, migrate directionally, then divide and organize into functional capillaries invested by a new basal lamina.

Posterior segment neovascularization (NV) is the vision-threatening pathology responsible for the two most common causes of acquired blindness in developed countries: exudative age-related macular degeneration (wet AMD) and proliferative diabetic retinopathy (PDR). Currently there are several approved treatments in the United States for treating the posterior segment NV that occurs during wet AMD. Laser photocoagulation involves thermal destruction of the neovascular lesion with a laser, which because of the vagaries of laser targeting and thermal energy transfer leads to collateral destruction of some surrounding tissue. Photodynamic therapy with Visudyne® solution involves intravenous administration of the solution to the patient, after which time a red laser is shone into the AMD-affected eye(s). The resultant photon absorption by the porphyrin active ingredient produces an electronically excited state that transfers energy to oxygen to produce reactive oxygen species. Use of strictly pharmacological therapies commenced in late 2004 with the approval in the United States of the VEGF-binding aptamer pegaptanib sodium (Macugen® solution) for the treatment of wet AMD. Surgical interventions with vitrectomy and membrane removal are the only options currently available for patients with proliferative diabetic retinopathy. Other pharmacologic treatment being evaluated clinically for the treatment of wet AMD and for diabetic retinopathy include anecortave acetate (Alcon, Inc.) and rhuFabV2 (Genentech) for AMD and LY333531 (Lilly) and Fluocinolone (Bausch & Lomb) for diabetic macular edema.

Non-exudative (dry) AMD can progress to wet AMD as described below. In a normally functioning retina, photoreceptors are supported by specialized cells in the retinal pigmented epithelium (RPE). These RPE cells take up released 11-trans retinaldehyde (in the form of the reduced retinol) and isomerize the olefin geometry back to the photoactive 11-cis form. RPE cells also phagocytose photoreceptor outer membrane segments that are continuously shed and replaced. Choroidal capillaries provide nutritional support (oxygen, proteins, hormones, etc.) to and remove waste products from photoreceptors and RPE cells, and are separated from them by Bruch's membrane. It is believed that a normally functioning Bruch's membrane is sufficiently permeable to allow diffusional exchange of nutrition and waste products between the choroidal capillaries and RPE cells. In dry AMD there is increased deposition of insoluble material within Bruch's membrane, leading to protein cross-linking. The accumulation of hydrophobic material may be a consequence of inefficient phagocytosis, and may precipitate an inflammatory response. Over time the membrane thickens and consequently has decreased permeability both to oxygen (and plasma-borne nutrients) from the choroidal capillaries and to waste products from RPE cells. RPE cells may die from the resulting metabolic distress. Without their RPE support cells, the associated photoreceptors in the macula die. This loss of macular photoreceptors is termed geographic atrophy. As the photoreceptors die, central visual acuity is gradually lost. Additionally, RPE cells may respond to the hypoxic condition resulting from Bruch's membrane thickening by secreting pro-angiogenic proteins in an attempt to re-establish adequate blood flow. The most important of these proteins is vascular endothelial growth factor (VEGF). VEGF promotes the proliferation of new capillaries from existing ones, and these breach Bruch's membrane. This leads to macular accumulation of fluid and blood from the leaky new vessels (VEGF is a potent blood vessel permeability-increasing factor) and formation of fibrous deposits and scar tissue in the retina, rapidly causing retinal detachment and therefore loss of visual function. Thus treating dry AMD by rescuing RPE cells from metabolic distress-induced cell death should also inhibit disease progression to wet AMD.

With respect to diabetic retinopathy, in addition to changes in the retinal microvasculature induced by hyperglycemia in diabetic patients leading to macular edema, proliferation of neovascular membranes is also associated with vascular leakage and edema of the retina. Where edema involves the macula, visual acuity decreases. In diabetic retinopathy, macular edema is the major cause of vision loss. Like angiogenic disorders, laser photocoagulation is used to stabilize or resolve the edematous condition. While reducing further development of edema, laser photocoagulation is a cytodestructive procedure, that, unfortunately will decrease vision in the affected eye.

A pharmacologic therapy for ocular NV and edema would provide substantial efficacy to the patient, in many diseases thereby avoiding invasive surgical or damaging laser procedures. Effective treatment of the NV and edema would improve the patient's quality of life and productivity within society. Also, societal costs associated with providing assistance and health care to the blind could be dramatically reduced.

Excessive angiogenesis of the blood vessels in the synovial lining of the joints is thought to play an important role in rheumatoid arthritis. In addition to forming new vascular networks, the endothelial cells release factors and reactive oxygen species that lead to pannus growth and cartilage destruction. It is believed that the factors involved in angiogenesis can actively contribute to, and help maintain, the chronically inflamed state of rheumatoid arthritis. It is believed that factors associated with angiogenesis can also have a role in osteoarthritis. The activation of the chondrocytes by angiogenic-related factors contributes to the destruction of the joint. At a later stage, the angiogenic factors can promote new bone formation.

Often times, cancer is associated with angiogenesis and is identified by solid tumor formation and metastasis. A tumor cannot expand without a blood supply to provide nutrients and remove cellular wastes. Tumors in which angiogenesis is important include solid tumors, and benign tumors such as acoustic neuroma, neurofibroma, trachoma and granulomas. Prevention or inhibition of angiogenesis could prevent or halt the growth of these tumors and the subsequent degenerative condition due to the presence of the tumor.

Angiogenesis has also been associated with blood-born tumors including leukemias, any of the various acute or chronic neoplastic diseases of bone marrow in which unrestrained proliferation of white blood cells occurs, usually accompanied by anemia, impaired blood clotting, and enlargement of the lymph nodes, liver, and spleen. It is believed that angiogenesis is significant as a caustive factor in the abnormalities in the bone marrow that give rise to leukemia-like tumors.

Angiogenesis is important in two stages of tumor metastasis. The first stage where angiogenesis stimulation is important is in the vascularization of the tumor which allows tumor cells to enter the blood stream and to circulate throughout the body. Once the tumor cells leave the primary site, and find a secondary metastasis site, angiogenesis must occur before the new tumor can grow and expand. Therefore, prevention of angiogenesis could prevent metastasis of tumors and contain the cancerous growth to the primary site.

Many individuals suffer from heart disease caused by a partial blockage of the blood vessels that supply the heart with nutrients. More severe blockage of blood vessels in such individuals often leads to hypertension, ischemic injury, stroke, or myocardial infarction. Typically vascular occlusion is preceded by vascular stenosis resulting from intimal smooth muscle cell hyperplasia. The underlying cause of the intimal smooth muscle cell hyperplasia is vascular smooth muscle injury and disruption of the integrity of the endothelial lining. Restenosis is a process of smooth muscle cell migration and proliferation at the is site of percutaneous transluminal coronary balloon angioplasty, which hampers the success of angioplasty. For both vascular stenosis and restenosis secondary to balloon angioplasty, the overall disease process can be termed a hyperproliferative vascular disease because of the etiology of the disease process.

There are many agents known to inhibit angiogenesis. For example, steroids functioning to inhibit angiogenesis in the presence of heparin or specific heparin fragments are disclosed in Crum, et al., A New Class of Steroids Inhibits Angiogenesis in the Presence of Heparin or a Heparin Fragment, Science, Vol. 230:1375-1378, Dec. 20, 1985. The authors refer to such steroids as "angiostatic" steroids. Included within this class of steroids found to be angiostatic are the dihydro and tetrahydro metabolites of cortisol and cortexolone. In a follow-up study directed to testing a hypothesis as to the mechanism by which the steroids inhibit angiogenesis, it was shown that heparin/angiostatic steroid compositions cause dissolution of the basement membrane scaffolding to which anchorage dependent endothelia are attached resulting in capillary involution; see, Ingber, et al., A Possible Mechanism for Inhibition of Angiogenesis by Angiostatic Steroids: Induction of Capillary Basement Membrane Dissolution, Endocrinology Vol. 119:1768-1775, 1986.

A group of tetrahydro steroids useful in inhibiting angiogenesis is disclosed in U.S. Pat. No. 4,975,537, Aristoff, et al. The compounds are disclosed for use in treating head trauma, spinal trauma, septic or traumatic shock, stroke, and hemorrhage shock. In addition, the patent discusses the utility of these compounds in embryo implantation and in the treatment of cancer, arthritis, and arteriosclerosis. Some of the steroids disclosed in Aristoff et al. are disclosed in U.S. Pat. No. 4,771,042 in combination with heparin or a heparin fragment for inhibiting angiogenesis in a warm blooded animal.

Compositions of hydrocortisone, "tetrahydrocortisol-S," and U-72,745G, each in combination with a beta cyclodextrin, have been shown to inhibit corneal neovascularization: Li, et al., Angiostatic Steroids Potentiated by Sulphated Cyclodextrin Inhibit Corneal Neovascularization, Investigative Ophthalmology and Visual Science, Vol. 32(11):2898-2905, October, 1991. The steroids alone reduce neovascularization somewhat but are not effective alone in effecting regression of neovascularization.

Tetrahydrocortisol (THF) has been disclosed as an angiostatic steroid in Folkman, et al., Angiostatic Steroids, Ann. Surg., Vol. 206(3), 374-383, 1987, wherein it is suggested angiostatic steroids may have potential use for diseases dominated by abnormal neovascularization, including diabetic retinopathy, neovascular glaucoma, and retrolental fibroplasia.

It has been previously shown that certain nonsteroidal anti-inflammatory drugs (NSAIDs) can inhibit angiogenesis and vascular edema in pathologic conditions. The ability of most NSAIDs to influence vascular permeability, leading to edema, and angiogenesis appears to be associated with their ability to block the cyclo-oxygenase enzymes (COX-1 and -2). Blockade of COX-1 and -2 is associated with a decrease in inflammatory mediators, such as $PGE_2$. Moreover, it appears that $PGE_2$ inhibition results in decreased expression and production of various cytokines including vascular endothelial growth factor (VEGF). VEGF is known to produce vascular leakage and angiogenesis in the eye of preclinical models. Also, increased levels of VEGF have been found in neovascular tissues and extracellular fluid from the eyes of patients with diabetic retinopathy and age-related macular degeneration. Thus, NSAIDs may inhibit vascular leakage and angiogenesis by modulating $PGE_2$ levels and its effects on VEGF expression and activity. This theory is supported by work involving animal tumor models which demonstrate that systemic administration of COX-2 inhibitors decreases $PGE_2$ and VEGF tissue levels and thereby prevents tumor-induced angiogenesis. In these models, VEGF activity and angiogenesis are restored by adding exogenous $PGE_2$ during continued COX-2 blockade. However, NSAIDs appear to have variable activity in animal models of ocular neovascularization (NV), in that selective COX inhibitors do not appear to inhibit choroidal neovascularization. In fact, these studies have called into question the role of COX-1 and/or COX-2 in the development of CNV.

As described in commonly owned U.S. application Ser. No. 09/929,381, it was found that certain 3-benzoylphenylacetic acids and derivatives, which are NSAIDs, are useful for treating angiogenesis-related disorders.

Lee et. al. have disclosed that compounds 1 and 2 inhibit $LTB_4$-induced chemotaxis of neutrophils as potently as lipoxin $A_4$ [Lee et. al., *Biochemical and Biophysical Research Communications* 1991, 180(3), 1416-21]. It is unclear if 1 and 2 act via activation of the lipoxin $A_4$ receptor (ALXR), as the authors did not attempt to reverse their chemotaxis inhibition using an ALXR antibody or small molecule functional antagonist. No other biological data for compounds 1 or 2 has appeared in the art.

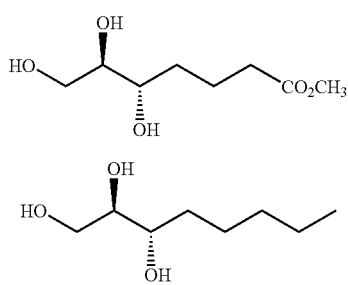

1

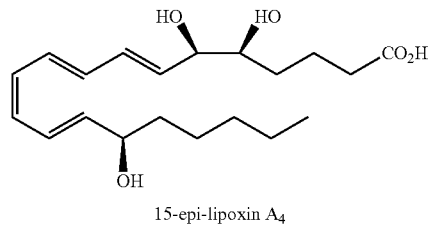

2

Lipoxin A₄ and certain analogs thereof have been reported to be anti-inflammatory agents (see for example Serhan et. al., U.S. Pat. No. 5,441,951). It has been reported that aspirin treatment of activated leukocytes induces the biosynthesis of 15-epi-lipoxin A₄ (aspirin-triggered lipoxin or ATL) from arachidonic acid, by converting the cyclooxygenase activity of the COX-2 isozyme into lipoxygenase activity [Serhan, Charles N. et. al., *J. Pharmacol. Exp. Ther.* 1998, 287, 779; Serhan, Charles N. et. al. *Clin. Chem. Lab. Med.* 1999, 37, 299].

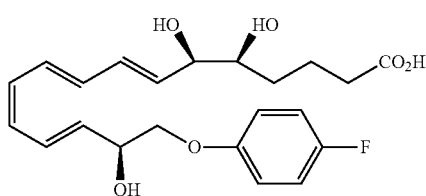

15-epi-lipoxin A₄

Aspirin has also been associated with anti-cancer [*Current Topics in Pharmacology* 2002, 6, 25-39; *Nature Medicine* (New York) 1999, 5(12), 1348-1349] and anti-angiogenesis effects, which may occur partly through the intermediacy of ATL [*Anticancer Research* 2001, 21(6A), 3829-3837; JP 08268886 A2 (CAN 126:65396); the use of aspirin in combination with the diphenylcyanopentenoic acid, satigrel, for treating diabetic retinopathy is also disclosed in this application]. Lipoxin analog 3 has been shown to inhibit both VEGF- and leukotriene D₄-induced endothelial cell chemotaxis and proliferation in vitro, and to inhibit VEGF-induced angiogenesis in a murine chronic granulomatous air pouch model in vivo [Fierro et al., *J. Pharm. Expt. Ther.* 2002, 300(2), 385-392].

3

The use of lipoxin A₄ and certain analogs, including 3, for treating angiogenesis-dependent diseases, including ocular neovascular diseases such as age-related macular degeneration and diabetic retinopathy, has been disclosed (Serhan and Fierro, U.S. Pat. No. 6,627,658 B1). However to the best of our knowledge no compounds of formula I have been claimed for posterior segment ocular disorders such as AMD and diabetic retinopathy or cellular hyperproliferative and angiogenesis-dependent diseases such as cancer, rheumatoid arthritis, and coronary artery restenosis after balloon angioplasty.

SUMMARY OF THE INVENTION

The present invention is directed to the use of 5,6,7-trihydroxyheptanoic acid and analogs to treat persons suffering from ocular posterior segment ocular disorders, such as dry AMD; ocular posterior segment neovascular and edematous disorders such as diabetic retinopathy and wet AMD; and diseases characterized by cellular hyperproliferation or excessive angiogenesis, such as rheumatoid arthritis, cancer, and vascular restenosis secondary to a percutaneous transluminal coronary angioplasty procedure.

DETAILED DESCRIPTION OF THE INVENTION

The compounds of the claimed invention are useful for the treatment of dry AMD and as inhibitors of cellular hyperproliferation, such as occurs during pathological angiogenesis. One aspect of the present invention pertains to methods for the prevention, reduction, or inhibition of angiogenesis. The method is accomplished by the administration of an effective amount of one or more compounds of the 5,6,7-trihydroxyhepatanoic acid class, and pharmaceutically acceptable salts, esters, amides or prodrugs thereof, to a subject in need thereof. As a consequence of the action of the therapeutic agent, dry AMD or angiogenesis is prevented or inhibited in the subject.

Another aspect of the present invention pertains to treatment of a dry AMD-affected patient with one or more 5,6,7-trihydroxyheptanoic acid analogs of the present invention. These compounds are also useful for slowing the progression of dry AMD to wet AMD.

Another aspect of the present invention pertains to treatment of an ocular neovascular or edematous disorder, by treatment of the affected patient with one or more 5,6,7-trihydroxyheptanoic acid analogs of the present invention. The compounds of the present invention are particularly useful for treating wet AMD and diabetic retinopathy and their associated sequellae, such as diabetic macular edema. Other ocular neovascularization-dependent diseases that may be treated in a human patient with one or more 5,6,7-trihydroxyheptanoic acid analogs of the present invention include chronic glaucoma, retinal detachment, sickle cell retinopathy, age-related macular degeneration, rubeosis iritis, uveitis, neoplasms, Fuch's heterochromic iridocyclitis, neovascular glaucoma, corneal neovascularization, neovascularization resulting from combined vitrectomy and lensectomy, retinal ischemia, choroidal vascular insufficiency, choroidal thrombosis, carotid artery ischemia, contusive ocular injury, retinopathy of prematurity, retinal vein occlusion, proliferative vitreoretinopathy, corneal angiogenesis, and retinal microvasculopathy Another aspect of the present invention pertains to treatment and prevention of rheumatoid and osteoarthritis, by treatment of the affected patient with one of more 5,6,7-trihydroxyheptanoic acid analogs of the present invention.

Another aspect of the present invention pertains to methods for the prevention or inhibition of solid tumor tissue growth undergoing neovascularization in a subject. The method is accomplished by the administration of an effective amount of one or more compounds of the 5,6,7-trihydroxyhepatanoic acid class, and pharmaceutically acceptable salts, esters, amides or prodrugs thereof, to a subject in need thereof.

Another aspect of the present invention pertains to inhibition, reduction, or prevention of vascular stenosis or restenosis secondary to a percutaneous transluminal coronary angioplasty procedure, by treatment of the affected patient with one of more 5,6,7-trihydroxyheptanoic acid analogs of the present invention. For prevention of restenosis these compounds can be administered preferably either orally, via intravenous injection, or using a drug-impregnated stent. For oral or intravenous delivery, treatment of the affected patient can commence several days before the operation or after the angioplasty procedure for from about 2 to about 28 days, and more typically for about the first 14 days following the procedure.

5,6,7-Trihydroxyheptanoic acid analogs useful for the methods of the present invention are those of formula I:

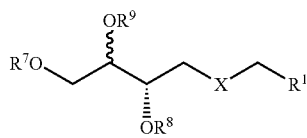

wherein:

$R^1$ is $C_2H_5$, $CO_2R$, $CONR^2R^3$, $CH_2OR^4$, or $CH_2NR^5R^6$;

R is H, $C_1$-$C_6$ straight chain or branched alkyl, $C_3$-$C_6$ straight chain or branched alkenyl, $C_3$-$C_6$ straight chain or branched alkynyl, $C_3$-$C_6$ cycloalkyl, or phenyl; or $R^1$ is a carboxylate salt of formula $CO_2^-R^+$, where $R^+$ is $Li^+$, $Na^+$, $K^+$, or an ammonium moiety of formula $^+NR^{10}R^{11}R^{12}R^{13}$, where $R^{10}$, $R^{11}$, $R^{12}$, and $R^{13}$ are independently H or $C_1$-$C_6$ straight chain or branched alkyl, each alkyl group optionally bearing an OH or $OCH_3$ substituent;

$R^2$, $R^3$ are independently H, $C_1$-$C_6$ straight chain or branched alkyl, $C_3$-$C_6$ straight chain or branched alkenyl, $C_3$-$C_6$ straight chain or branched alkynyl, $C_3$-$C_6$ cycloalkyl, benzyl, phenyl, OH, $OCH_3$, or $OC_2H_5$, provided that at most only one of $R^2$, $R^3$ is OH, $OCH_3$, or $OC_2H_5$;

$R^4$ is H, $C(O)R^{14}$, $C_1$-$C_6$ straight chain or branched alkyl, $C_3$-$C_6$ straight chain or branched alkenyl, $C_3$-$C_6$ straight chain or branched alkynyl, $C_3$-$C_6$ cycloalkyl benzyl, or phenyl;

$R^5$, $R^6$ are independently H, $C(O)R^{14}$ $C_1$-$C_6$ straight chain or branched alkyl, $C_3$-$C_6$ straight chain or branched alkenyl, $C_3$-$C_6$ straight chain or branched alkynyl, $C_3$-$C_6$ cycloalkyl, benzyl, phenyl, OH, $OCH_3$, or $OC_2H_5$, provided that at most only one of $R^5$, $R^6$ is OH, $OCH_3$, or $OC_2H_5$;

X is O, $CH_2$, or S;

$R^7$, $R^8$, and $R^9$ are independently H, $CH_3$, $C_2H_5$, $C(O)R^{14}$, $C(O)NR^{14}R^{15}$, or $CO_2R^{15}$;

or $R^7$ and $R^8$ or $R^8$ and $R^9$ together constitute a carbonyl group (C=O), thus forming a cyclic carbonate;

or $OR^8R^1$ together form a cyclic ester (a lactone);

$R^{14}$ and $R^{15}$ are H, $C_1$-$C_6$ straight chain or branched alkyl, $C_3$-$C_6$ straight chain or branched alkenyl, $C_3$-$C_6$ straight chain or branched alkynyl, $C_3$-$C_6$ cycloalkyl, benzyl, or phenyl; and indicates that the $OR^9$ substituent can be arranged to afford the R or S absolute configuration at that position:

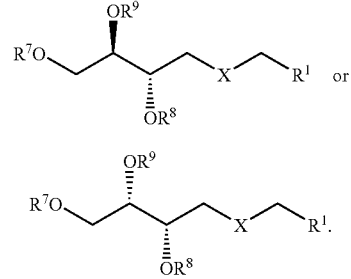

Preferred for methods of use of this invention are those compounds of formula I wherein:

$R^1$ is $C_2H_5$, $CO_2R$, $CH_2OR^4$, or a carboxylate salt of formula $CO_2^-R^+$;

$R^+$ is $Li^+$, $Na^+$, $K^+$, or $NH_4^+$;

R is H, $CH_3$, $C_2H_5$, n-$C_3H_7$, or i-$C_3H_7$X is $CH_2$;

X is $CH_2$;

$R^4$ is H, $COCH_3$, or $CH_3$; and $R^7$, $R^8$, $R^9$ are independently H, $CH_3$, $CH_3CO$;

or $R^7$ and $R^8$ or $R^8$ and $R^9$ together constitute a carbonyl group (C=O), thus forming a cyclic carbonate;

or $OR^8R^1$ together form a cyclic ester (a lactone).

Among the especially preferred are compounds 1-6. Compound 1 is commercially available from Biomol Research Laboratories, Plymouth Meeting, Pa., and compound 2 can be prepared as detailed in Lee et. al., *Biochemical and Biophysical Research Communications* 1991, 180(3), 1416-21. Compounds 3-6 can be prepared as described in examples 1-4 below.

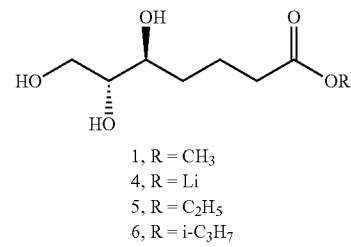

1, R = $CH_3$
4, R = Li
5, R = $C_2H_5$
6, R = i-$C_3H_7$

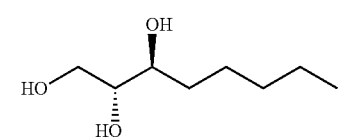

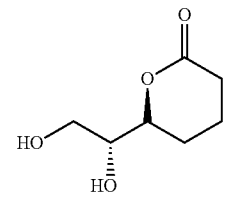

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Synthesis of Compound 3

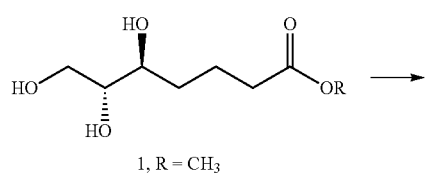

1, R = CH₃

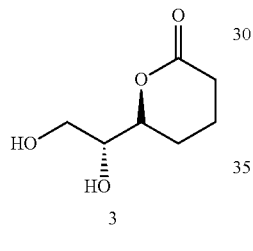

3

A solution of methyl ester 1 (20 mg, 0.104 mmol) in MeOH (2.1 mL) containing 1 M LiOH (0.5 mL, 0.5 mmol) was heated in a microwave heater at 120° C. for 6 minutes. The reaction was concentrated and the residue was chromatographed on a 10 mm diameter×18 cm tall C18 reverse-phase silica gel column eluting with 7:3 v:v 0.05 M HCl:acetonitrile to afford a crude white solid after concentration (40.9 mg). The solid was rinsed with hot CH₃CN (2×2 mL) and the filtrate was concentrated to afford lactone 3 (7.8 mg, 47%). ¹³C NMR (150 MHz, dmso-d₆) δ 171.12 (C), 79.86 (CH), 72.44 (CH), 62.03 (CH₂), 29.39 (CH₂), 21.67 (CH₂), 17.55 (CH₂).

Example 2

Synthesis of Compound 4

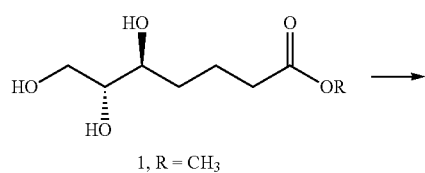

1, R = CH₃

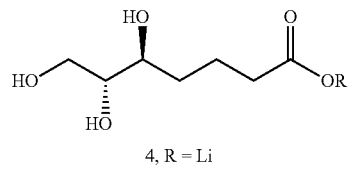

4, R = Li

A solution of methyl ester 1 in aqueous MeOH is heated to reflux in the presence of 3 equivalents of lithium hydroxide. After 6 h the reaction is cooled to room temperature and the pH of the solution is adjusted to 6 by the addition of 70-9 mesh sulfonic acid resin MP (commercially available from Novabiochem/EMD Biosciences, 10394 Pacific Center Court, San Diego, Calif. 92121). The solution is filtered through a 0.2 μM poly-terfluoroethylene syringe filter and concentrated to afford the lithium carboxylate 4 as a white solid. ¹H NMR (D₂O, 400 MHz) δ 3.69-3.64 (m, 1H), 3.55-3.47 (m, 3H), 2.16-2.12 (m, 2H), 1.67-1.64 (m, 1H), 1.54-1.48 (m, 2H), 1.38-1.34 (m, 1H). ¹³C NMR (D₂O, 100 MHz) δ 183.46 (C), 74.61 (CH), 71.67 (CH), 62.49 (CH₂), 37.26 (CH₂), 31.55 (CH₂), 22.04 (CH₂).

Example 3

Synthesis of Compound 8

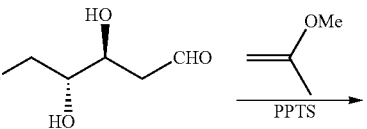

2-deoxy-D-ribose

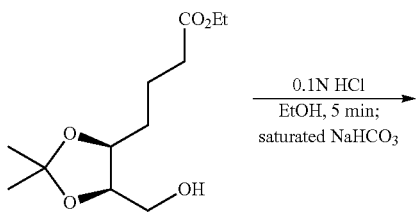

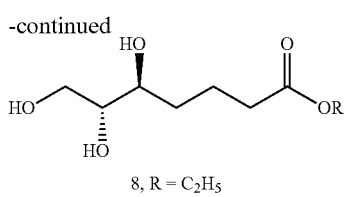

8, R = C₂H₅

2-deoxy-D-ribose is converted to the acetonide-protected lactol 10 by treatment with 2-methoxypropene and catalytic pyridinium p-toluenesulfonate (PPTS) in ethyl acetate. Wittig reaction with Ph₃P=CHCO₂Et in THF in the presence of catalytic benzoic acid affords enoate 11, which is reduced to 12 under a hydrogen atmosphere in the presence of catalytic Pd/C in ethanol. Deprotection of 12 using 0.1 N HCl in ethanol for 5 minutes, followed by quenching with aqueous NaHCO₃, affords 8 after silica gel chromatographic purification.

Example 4

Synthesis of Compound 9

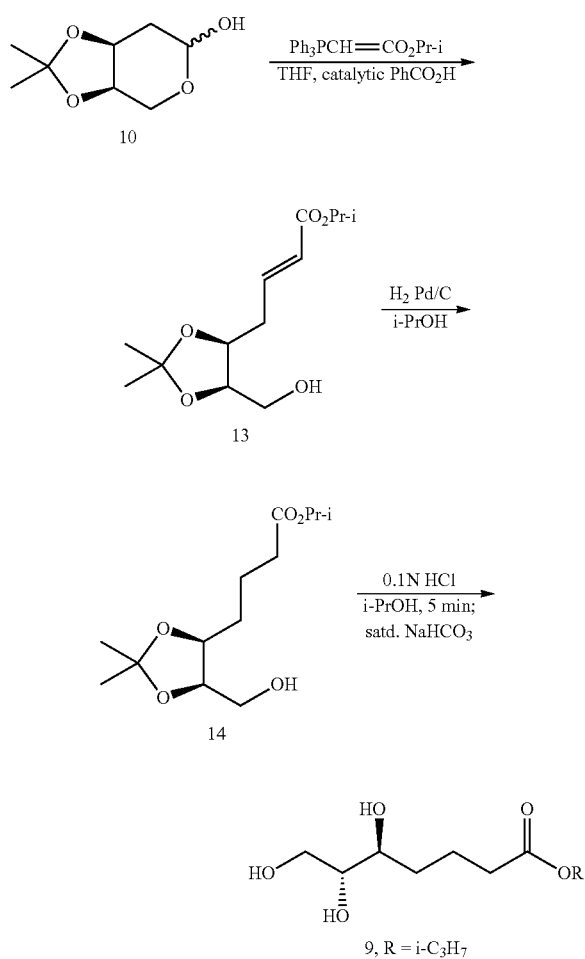

9, R = i-C₃H₇

Wittig reaction of lactol 10 with Ph₃P=CHCO₂Et in THF in the presence of catalytic benzoic acid affords enoate 13, which is reduced to 14 under a hydrogen atmosphere in the presence of catalytic Pd/C in isopropanol. Deprotection of 14 using 0.1 N HCl in isopropanol for 5 minutes, followed by quenching with aqueous NaHCO₃, affords 9 after silica gel chromatographic purification.

The present invention is also directed to compositions containing 5,6,7-trihydroxyheptanoic acid and analogs and methods for their use. According to the methods of the present invention, a composition comprising one or more compounds of the present invention and a pharmaceutically acceptable carrier for systemic or local administration is administered to a mammal in need thereof. The compositions are formulated in accordance with methods known in the art for the particular route of administration desired.

The compounds of the present invention can be administered either systemically or locally. Systemic administration includes: oral, transdermal, subdermal, intraperitoneal, subcutaneous, transnasal, sublingual, or rectal. Local administration for ocular administration includes: topical, intravitreal, periocular, transcleral, retrobulbar, sub-tenon, or via an intraocular device. Preferred administration depends on the type of ocular neovascular condition or disease being treated.

The compositions administered according to the present invention comprise a pharmaceutically effective amount of one or more compounds. As used herein, a "pharmaceutically effective amount" is one which is sufficient to reduce or prevent neovascularization and/or edema. Generally, for compositions intended to be administered systemically for the treatment of ocular neovascularization or edema, cancer, arthritis, or vascular restenosis secondary to cardiac angioplasty, the total amount of compound will be about 0.01-100 mg/kg.

Included within the scope of the present invention are the individual enantiomers of the title compounds, as well as their racemic and non-racemic mixtures. Generally, the individual enantiomers can be procured by a number of methods, including but not limited to: enantioselective synthesis from the appropriate enantiomerically pure or enriched starting material; synthesis from racemic/non-racemic or achiral starting materials using a chiral reagent, catalyst, solvent, etc. (see for example: *Asymmetric Synthesis*, J. D. Morrison and J. W. Scott, Eds. Academic Press Publishers, (New York) 1985), volumes 1-5; *Principles of Asymmetric Synthesis*, R. E. Gawley and J. Aube, Eds.; Elsevier Publishers (Amsterdam 1996)); and isolation from racemic and non-racemic mixtures by a number of known methods, e.g. by purification of a sample by chiral HPLC (*A Practical Guide to Chiral Separations by HPLC*, G. Subramanian, Ed., VCH Publishers, (New York 1994); *Chiral Separations by HPLC*, A. M. Krstulovic, Ed., Ellis Horwood Ltd. Publishers (1989)), or by enantioselective hydrolysis of a carboxylic acid ester sample by an enzyme (Ohno, M.; Otsuka, M., *Organic Reactions*, 37:1 (1989)). Those skilled in the art will appreciate that racemic and non-racemic mixtures may be obtained by several means, including without limitation, nonenantioselective synthesis, partial resolution, or even mixing samples having different enantiomeric ratios. Departures may be made from such details within the scope of the accompanying claims without departing from the principles of the invention and without sacrificing its advantages. Also included within the scope of the present invention are the individual isomers substantially free of their respective enantiomers.

The following topical ophthalmic and systemic formulations are useful according to the present invention administered 1-4 times per day according to the discretion of a skilled clinician.

Example 5

| Ingredients | Amount (wt %) |
| --- | --- |
| Compound of formula I, especially Compound 1 | 0.01-2% |
| Hydroxypropyl methylcellulose | 0.5% |
| Dibasic sodium phosphate (anhydrous) | 0.2% |
| Sodium chloride | 0.5% |
| Disodium EDTA (Edetate disodium) | 0.01% |
| Polysorbate 80 | 0.05% |
| Benzalkonium chloride | 0.01% |
| Sodium hydroxide/Hydrochloric acid | For adjusting pH to 7.3-7.4 |
| Purified water | q.s. to 100% |

Example 6

| Ingredients | Amount (wt %) |
| --- | --- |
| Compound of formula I, especially Compound 4 | 0.01-2% |
| Methyl cellulose | 4.0% |
| Dibasic sodium phosphate (anhydrous) | 0.2% |
| Sodium chloride | 0.5% |
| Disodium EDTA (Edetate disodium) | 0.01% |
| Polysorbate 80 | 0.05% |
| Benzalkonium chloride | 0.01% |
| Sodium hydroxide/Hydrochloric acid | For adjusting pH to 7.3-7.4 |
| Purified water | q.s. to 100% |

Example 7

| Ingredients | Amount (wt %) |
| --- | --- |
| Compound of formula I, especially Compound 2 | 0.01-2% |
| Guar Gum | 0.4-6.0% |
| Dibasic sodium phosphate (anhydrous) | 0.2% |
| Sodium chloride | 0.5% |
| Disodium EDTA (Edetate disodium) | 0.01% |
| Polysorbate 80 | 0.05% |
| Benzalkonium chloride | 0.01% |
| Sodium hydroxide/Hydrochloric acid | For adjusting pH to 7.3-7.4 |
| Purified water | q.s. to 100% |

Example 8

| Ingredients | Amount (wt %) |
| --- | --- |
| Compound of formula I, especially Compound 3 | 0.01-2% |
| White petrolatum and mineral oil and lanolin | Ointment consistency |
| Dibasic sodium phosphate (anhydrous) | 0.2% |
| Sodium chloride | 0.5% |
| Disodium EDTA (Edetate disodium) | 0.01% |
| Polysorbate 80 | 0.05% |
| Benzalkonium chloride | 0.01% |
| Sodium hydroxide/Hydrochloric acid | For adjusting pH to 7.3-7.4 |

Example 9

| 10 mM IV Solution w/v % | |
| --- | --- |
| Compound of formula I, especially Compound 4 | 0.384% |
| L-Tartaric acid | 2.31% |
| Sodium hydroxide | pH 3.8 |
| Hydrochloric acid | pH 3.8 |
| Purified water | q.s. to 100% |

Example 10

| 5 mg Capsules | |
| --- | --- |
| Ingredient | mg/capsule (Total Wt. 100 mg) |
| Compound of formula I, especially Compound 4 | 5 |
| Lactose, anhydrous | 55.7 |
| Starch, Sodium carboxy-methyl | 8 |
| Cellulose, microcrystalline | 30 |
| Colloidal silicon dioxide | .5 |
| Magnesium stearate | .8 |

The preferred compositions of the present invention are intended for administration to a human patient suffering from: dry AMD; an ocular NV or edematous disease or disorder, such as, diabetic retinopathy, chronic glaucoma, retinal detachment, sickle cell retinopathy, age-related macular degeneration, rubeosis iritis, uveitis, neoplasms, Fuch's heterochromic iridocyclitis, neovascular glaucoma, corneal neovascularization, neovascularization resulting from combined vitrectomy and lensectomy, retinal ischemia, choroidal vascular insufficiency, choroidal thrombosis, carotid artery ischemia, contusive ocular injury, retinopathy of prematurity, retinal vein occlusion, proliferative vitreoretinopathy, corneal angiogenesis, retinal microvasculopathy, and retinal (macular) edema; cancer; arthritis; and vascular restenosis secondary to a percutaneous transluminal coronary angioplasty procedure.

This invention has been described by reference to certain preferred embodiments; however, it should be understood that it may be embodied in other specific forms or variations thereof without departing from its special or essential characteristics. The embodiments described above are therefore considered to be illustrative in all respects and not restrictive, the scope of the invention being indicated by the appended claims rather than by the foregoing description.

We claim:
1. A method for treating persons suffering from dry AMD, which comprises administering a pharmaceutically effective amount of a compound selected from the group consisting of:
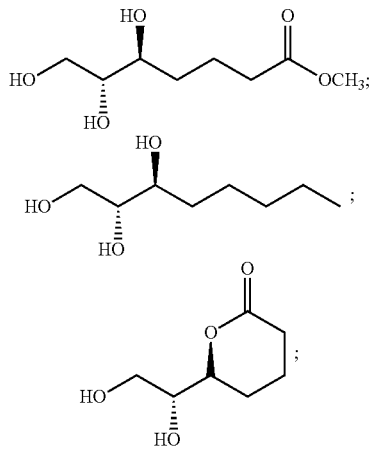
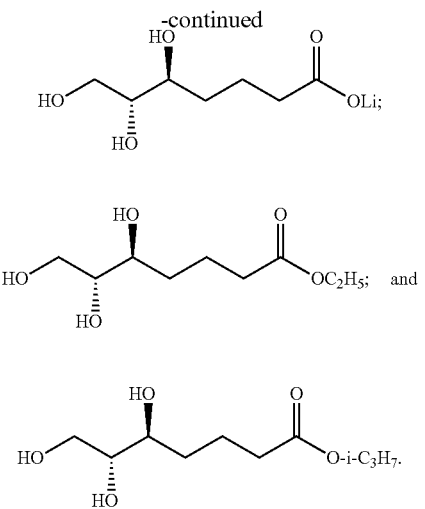
* * * * *